United States Patent [19]

Sprenger, deceased

[11] 3,994,955
[45] Nov. 30, 1976

[54] SUBSTITUTED PHENOXYDIALKYLACETIC ACIDS AND ESTERS

[75] Inventor: William K. Sprenger, deceased, late of Arlington Heights, Ill., by Barbara A. Sprenger, widow and personal representative

[73] Assignee: G. D. Searle & Co., Chicago, Ill.

[22] Filed: Jan. 20, 1975

[21] Appl. No.: 542,242

[52] U.S. Cl. .................. 260/473 G; 260/520 C; 424/308
[51] Int. Cl.² .......................... C07C 69/76
[58] Field of Search ............... 260/473 G, 520 C

[56] References Cited
UNITED STATES PATENTS
3,458,565  7/1969  Bicking et al. .................. 260/473 G

*Primary Examiner*—Paul J. Killos
*Attorney, Agent, or Firm*—John J. McDonnell

[57] ABSTRACT

The present invention encompasses compounds of the formula

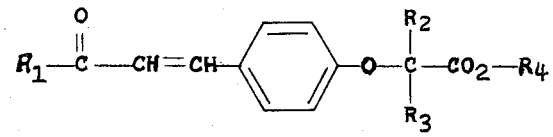

wherein $R_1$ is lower alkyl containing 1–7 carbon atoms, phenyl, halo(substituted)phenyl, phenyl, or lower alkoxy (substituted)phenyl containing 1–7 carbon atoms; $R_2$ and $R_3$ are lower alkyl containing 1–7 carbon atoms; and $R_4$ is hydrogen or lower alkyl containing 1–7 carbon atoms. The compounds of the present invention are prepared by the condensation of alkyl(4-formylphenoxy)-2,2-dialkyl acetate with an appropriate alkyl or aryl methyl/ketone in base. These compounds have antibiotic activity and in particular they are antifungal agents effective against *Trichophyton mentagrophytes*. Halophenyl members of the present invention are also effective hypolipemic agents.

2 Claims, No Drawings

SUBSTITUTED PHENOXYDIALKYLACETIC ACIDS AND ESTERS

The present invention encompasses compounds of the formula

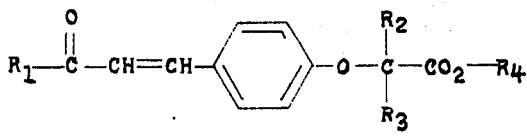

wherein $R_1$ is lower alkyl containing 1–7 carbon atoms, phenyl, halo(substituted)phenyl, lower alkyl (substituted) phenyl wherein the lower alkyl contains 1–7 carbon atoms, or lower alkoxy (substituted) phenyl wherein the lower alkoxy contains 1–7 carbon atoms; $R_2$ and $R_3$ are lower alkyl containing 1–7 carbon atoms; and $R_4$ is hydrogen or lower alkyl containing 1–7 carbon atoms.

Embodiments of the present invention wherein $R_1$ is lower alkyl containing 1–7 carbon atoms are exemplified by ethyl 2-[4-(2-propionylethenyl)phenoxy]-2,2-dimethylacetate and 2-[4-(2-acetylethenyl)phenoxy]-2,2-dimethylacetic acid.

Embodiments of the present invention wherein $R_1$ is phenyl or substituted phenyl are exemplified by 2-[4-(2-p-chlorobenzoylethenyl)phenoxy]-2,2-dimethylacetate and 2-[4-(2benzoylethenyl)phenoxy]-2,2-dimethylacetate.

Especially preferred embodiments of the present invention are those in which $R_1$ is halophenyl with 2-[4-(2-p-chlorobenzoylethenyl)phenoxy]-2,2-dimethylacetate being most preferred. This embodiment is preferred by virtue of hypolipemic activity of the members.

The compounds of the present invention are structurally distinct from compounds known in the most closely related art. For example, U.S. Pat. No. 3,558,612 describes 4-(arylcarbonylalkanyl)phenoxyacetic acid derivatives. The compounds of the present invention are particularly distinct from the compounds in the U.S. Pat. No. 3,558,612 in that the compounds in the present invention are derivatives of dialkyl acetic acid instead of acetic acid.

The compounds of the present invention are also structurally distinct from the compounds disclosed in U.S. Pat. No. 3,636,073 in that the former are only para-substituted in the phenyl ring and are derivatives of dialkylacetic acid and latter compounds have the following structure

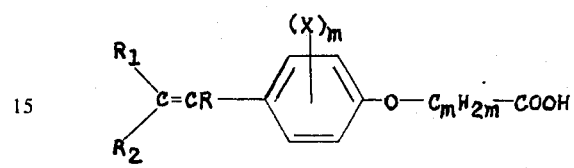

wherein R is hydrogen or alkyl, for example, lower alkyl such as methyl, ethyl, propyl, etc; $R_1$ is hydrogen, lower alkanoyl such as acetyl, propionyl, etc., cyano, carboxy, alkoxycarbonyl, for example, lower alkoxycarbonyl, methoxycarbonyl, ethoxycarbonyl, etc., sulfamoyl, carbamoyl, alkylsulfonyl, for example, lower alkylsulfonyl such as methanesulfonyl, ethanesulfonyl, etc. or mononuclear arylsulfonyl such as benzenesulfonyl, etc; $R_2$ is cyano, alkoxycarbonyl, for example, lower alkoxycarbonyl such as methoxycarbonyl, ethoxycarbonyl, X is halo and m is 2.

Compounds of the present invention wherein $R_1$ is halophenyl unexpectedly are potent hypolipemic agents. This unexpected hypolipemic activity is illustrated by the fact that compound A is a potent hypolipemic agent and compound B is inactive as a hypolipemic agent.

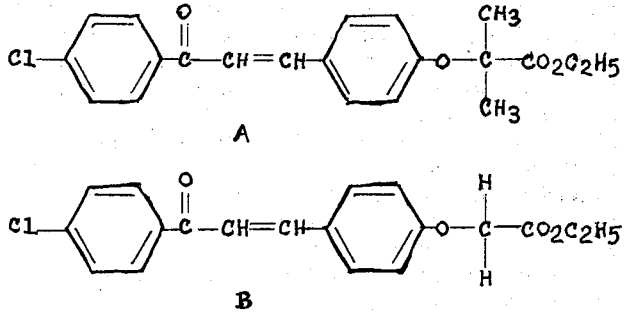

Evidently dialkyl substitution of the ethylacetate moiety significantly alters biological properties.

Compounds of the present invention are prepared as set out in Scheme I wherein $R_1$, $R_2$, $R_3$ and $R_4$ are as previously defined.

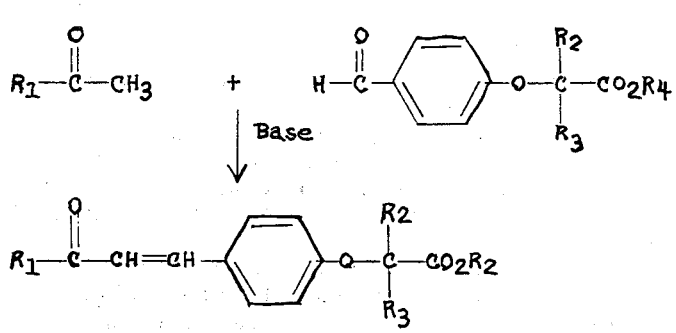

Scheme I

Thus, the condensation of alkyl(4-formylphenoxy) 2,2-dialkylacetate described in U.S. Pat. No. 3,842,120 with an appropriate alkyl or aryl methyl ketone in base provides compounds of the present invention.

In this manner 7.1 parts of ethyl (4-formylphenoxy) 2,2-dimethylacetate and 4.7 parts of p-chloroacetophenone in 10 parts by volume of ethanol containing .01 part of sodium metal are reacted for 2 hours. This reaction mixture if quenched with 100 parts of cold water and extracted with ether. The ether extracts are dried over magnesium sulfate. Filtration of the magnesium sulfate, removal of the ether by evaporation at reduced pressure and column chromatography on silica gel provides ethyl 2-[4-(2-p-chlorobenzoylethynyl)-phenoxy]-2,2-dimethylacetate, melting at 68°–70° C. Treatment of this ester with alcoholic potassium hydroxide for 2 hours, followed by extraction with ether, and acidification with dilute hydrochloric acid provides a precipitate which is 2-[4-(2-p-chlorobenzoyl)-phenoxy]-2,2-dimethylacetic acid.

This hypolipemic utility is demonstrated by the following standardized test for their capacity to lower both serum cholesterol and serum triglycerides in rats. Charles River CD rats weighing 400–450 gm. apiece and maintained on tap water ad libitum are used in this test. To each of a group (Group I) of 8 such animals is administered in the powdered diet 0.2% of compound. The compound is incorporated by dissolving it in acetone or other volatile solvent and mixing the solution with the diet, whereupon the solvent is allowed to evaporate at room temperatures. The animals are fed the treated diet for 5 days. On the 6th day serum samples are obtained and are analyzed for cholesterol and triglycerides. Cholesterol is analyzed by the method of Block et al., Automation in Analytical Chemistry, Technicon Symposium, 1965, Mediad Incorporated, White Plains, N. Y. 10601, pp. 345 ff.; and the triglycerides are assayed by the Procedure of Noble and Campbell, Clin. Chem., 16, 166 (1970). Controls are provided by a second group (Group II) of 8 animals each concurrently and identically treated except that in Group II the compound is omitted from the diet. A compound is considered hypolipemic if the mean mg. % serum cholesterol and triglyceride values for Group I are significantly lower than for Group II. The level of significance in each instance is $P < 0.05$ as determined by the Wilcoxon Rank Sum method.

The antifungal utility of the compound of the instant invention, in particular their activity against *Trichophyton mentagrophytes*, is demonstrated by methods set out in U.S. Pat. No. 3,679,697, at Column 2, lines 65–75 and Column 3, lines 1–13.

The following examples are presented to further illustrate the present invention. They should not be construed as limiting it either in spirit or in scope. In these examples quantities are indicated in parts by weight unless parts by volume are specified, and temperatures are indicated in degrees Centigrade (° C.). The relationship between parts by weight and parts by volume is the same as that existing between grams and milliliters.

EXAMPLE 1

7.1 Parts of ethyl (4-formylphenoxy)-2,2-dimethylacetate described in U.S. Pat. No. 3,842,120 and 4.7 parts of p-chloroacetophenone in 10 parts by volume of ethanol containing .01 part of sodium metal are reacted for 2 hours. This reaction mixture is quenched with 100 parts of cold water and extracted with ether. The ether extracts are dried over magnesium sulfate. Filtration of the magnesium sulfate, removal of the ether by evaporation at reduced pressure and column chromatography on silica gel provides ethyl 2-[4-(2-p-chlorobenzoylethenyl)phenoxy]-2,2-dimethylacetate, melting at 68–70° C. This compound has the following structural formula

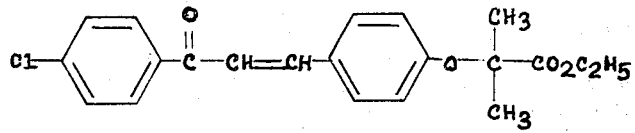

Treatment of the above ester with alcoholic potassium hydroxide for 2 hours, followed by estraction with ether, and acidification with dilute hydrochloric acid provides a precipitate which is 2-[4-(2-p-chlorobenzoyl)phenoxy]-2,2-dimethylacetic acid.

EXAMPLE 2

Following the procedure in Example 1 using 7.1 parts of ethyl 2-(4-formylphenoxy)-2-methyl-2-ethylacetate and 4.9 parts of p-bromoacetophenone in 10 parts by volume of ethanol containing 0.1 part of sodium metal provides ethyl 2-[4-(2-p-bromobenzoylethenyl)-phenoxy]-2,2-dimethylacetate. This compound has the following structural formula.

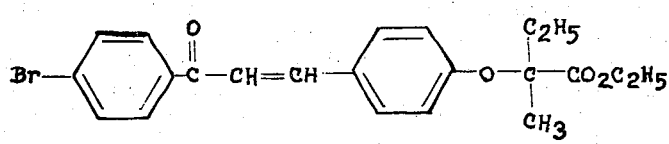

EXAMPLE 3

Following the procedure in Example 1 using 7.1 parts of ethyl 2-(4-formylphenoxy)-2,2-dimethylacetate and 4.7 parts of acetophenone in 10 parts by volume of ethanol containing 0.1 part of sodium metal provides 2-[4-(2-benzoylethenyl)phenoxy]-2,2-dimethylacetate. This compound has the following structural formula

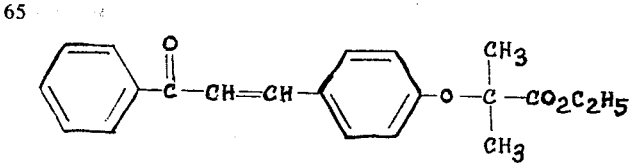

EXAMPLE 4

Following the procedure in Example 1 using 7.1 parts of ethyl 2-(f-formylphenoxy)-2,2-dimethylacetate and 4.9 parts of p-methylacetophenone in 10 parts by volume of ethanol containing 0.1 part of sodium metal provides ethyl 2-[4-(2-p-methylbenzoylethenyl)-phenoxy]-2,2-dimethylacetate. This compound has the following structural formula.

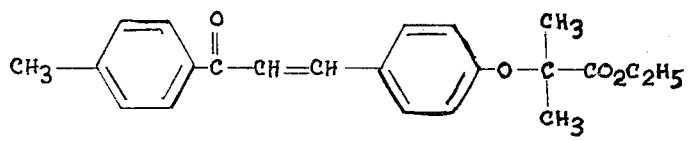

EXAMPLE 5

Following the procedure in Example 1 using 7.1 parts of ethyl 2-(4-formylphenoxy)-2,2-dimethylacetate and 4.9 parts of p-methoxyacetophenone in 10 parts by volume of ethanol containing 0.1 parts of sodium metal provides ethyl 2-[4-(2-p-methoxybenzoylethenyl)-phenoxy]-2,2-dimethylacetate. This compound has the following structural formula.

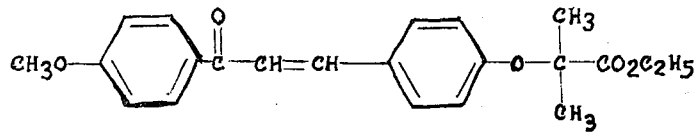

EXAMPLE 6

Following the procedure in Example 1 using 7.1 parts of methyl 2-(4-formylphenoxy)-2-methyl-2-ethylacetate and 4.9 parts of p-ethoxyacetophenone in 10 parts by volume of ethanol containing 0.1 part of sodium metal provides methyl 2-[4-(2-p-ethoxybenzoylethenyl)phenoxy]-2-methyl-2 ethylacetate. This compound has the following structural formula.

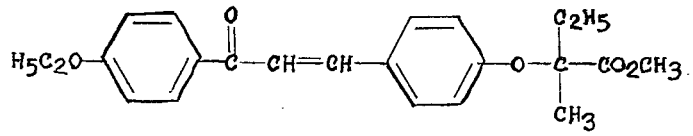

EXAMPLE 7

Following the procedure in Example 1 using 7.1 parts of ethyl 2-(4-formylphenoxy)-2,2-dimethylacetate and 4.9 parts of p-ethylacetophenone in 10 parts by volume of ethanol containing 0.1 part of sodium metal provides ethyl 2-[4-(2-p-ethylbenzoylethenyl)phenoxy]-2,2-dimethylacetate. This compound has the following structural formula

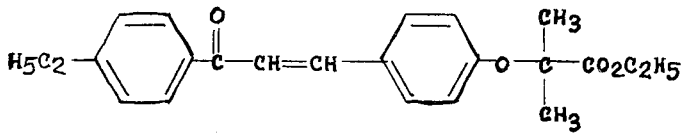

EXAMPLE 8

Following the procedure in Example 1 using 7.1 parts of ethyl 2-(4-formylphenoxy)-2,2-dimethylacetate and 4.5 parts of methyl ethyl ketone in 10 parts by volume of ethanol containing 0.1 part of sodium metal provides ethyl 2-[4-(2-propionylethynyl)phenoxy]-2,2-dimethylacetate as an oil (1.5522). This compound has the following structural formula.

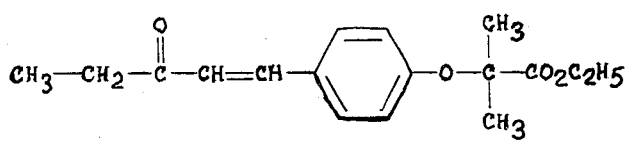

EXAMPLE 9

Following the procedure in Example 1 using 7.1 parts of ethyl 2-(4-formylphenoxy)-2,2-dimethylacetate and 5.0 parts of acetone in 10 parts by volume of ethanol containing 0.1 part of sodium metal provides ethyl 2-[4-(2-acetylethenyl)phenoxy]-2,2-dimethylacetate. This compound has the following structural formula.

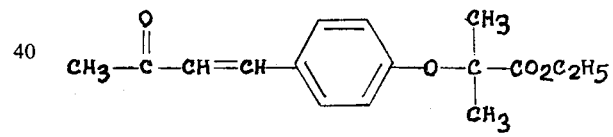

Hydrolysis of this ester in alcoholic potassium hydroxide provides 2-[4-(2-acetylethenyl)phenoxy[-2,2-dimethylacetic acid melting at 134°–135° C. This compound has the following structural formula.

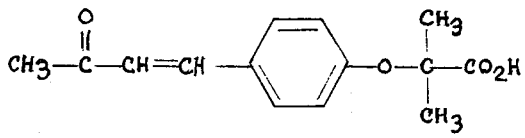

What is claimed is:
1. A compound of the formula
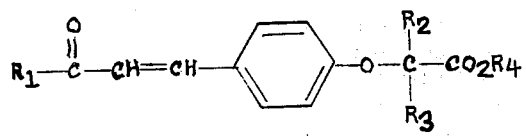
wherein $R_1$ is halo(substituted)phenyl, $R_2$ and $R_3$ are lower alkyl containing 1–7 carbon atoms and $R_4$ is hydrogen or lower alkyl containing 1–7 carbon atoms.
2. A compound according to claim 1 which is ethyl 2-[4-(2-p-chlorobenzoylethenyl)phenoxy]2,2-dimethylacetate.
* * * * *